United States Patent
Wen et al.

(10) Patent No.: US 9,797,976 B2
(45) Date of Patent: Oct. 24, 2017

(54) BIOSENSOR CALIBRATION SYSTEM AND RELATED METHOD

(71) Applicant: Taiwan Semiconductor Manufacturing Company, Ltd., Hsin-Chu (TW)

(72) Inventors: Chin-Hua Wen, Toufen Township (TW); Jui-Cheng Huang, Hsin-Chu (TW); Yi-Shao Liu, Zhubei (TW); Chun-Wen Cheng, Zhubei (TW); Tung-Tsun Chen, Hsin-Chu (TW)

(73) Assignee: TAIWAN SEMICONDUCTOR MANUFACTURING COMPANY (TW)

( * ) Notice: Subject to any disclaimer, the term of this patent is extended or adjusted under 35 U.S.C. 154(b) by 796 days.

(21) Appl. No.: 14/103,482

(22) Filed: Dec. 11, 2013

(65) Prior Publication Data
US 2015/0160323 A1 Jun. 11, 2015

(51) Int. Cl.
    *G01R 35/00* (2006.01)
    *G01N 27/414* (2006.01)

(52) U.S. Cl.
    CPC ......... *G01R 35/00* (2013.01); *G01N 27/4145* (2013.01)

(58) Field of Classification Search
None
See application file for complete search history.

(56) References Cited

U.S. PATENT DOCUMENTS

| | | | |
|---|---|---|---|
| 8,263,336 B2* | 9/2012 | Rothberg | G01N 27/4145 257/253 |
| 8,776,573 B2* | 7/2014 | Rearick | G06F 19/22 73/1.02 |
| 2005/0230245 A1* | 10/2005 | Morgenshtein | G01N 27/4148 204/416 |
| 2013/0211213 A1 | 8/2013 | DeHennis et al. | |

FOREIGN PATENT DOCUMENTS

TW     201339567     10/2013

OTHER PUBLICATIONS

Chen, Kuan-I et al., "Silicon nanowire field-effect transistor-based biosensors for biomedical diagnosis and cellular recording investigation," Nano Today, 2011, pp. 131-154, vol. 6, Elsevier Ltd.
Kim, Seong-Jin et al., "Label-Free CMOS Bio Sensor With On-Chip Noise Reduction Scheme for Real-Time Quantitative Monitoring of Biomolecules," IEEE Transactions on Biomedical Circuits and Systems, Jun. 2012, pp. 189-196, vol. 6, No. 3, IEEE.

(Continued)

*Primary Examiner* — An Do
*Assistant Examiner* — Renee I Wilson
(74) *Attorney, Agent, or Firm* — Sterne, Kessler, Goldstein & Fox P.L.L.C.

(57) ABSTRACT

A device includes a first biosensor of a biosensor array; a second biosensor of a biosensor array; a readout circuit electrically connected to the biosensor array; a decoder electrically connected to the biosensor array; a voltage generator electrically connected to the biosensor array; and a decision system electrically connected to the voltage generator and the readout circuit.

18 Claims, 8 Drawing Sheets

(56) References Cited

OTHER PUBLICATIONS

Lee, Byunghun, et al., "An Electronic DNA Sensor Chip using Integrated Capacitive Read-out Circuit," 32nd Annual International Conference of the IEEE EMBS, 2010, pp. 6547-6550, Buenos Aires, Argentina.

Lee, Kang-Ho, et al., "CMOS Capacitive Biosensor with Enhanced Sensitivity for Label-Free DNA Detection," 2012 IEEE International Solid-State Circuits Conference, Session 6, Medical, Displays, and Imagers, 6.6, pp. 120-122, Korea.

Nakazato, Kazuo, "An Integrated ISFET Sensor Array," Sensors, 2009, pp. 8831-8851, vol. 9, Japan.

* cited by examiner

| 10-1 | 10-2 | 10-3 | 10-4 |
|---|---|---|---|
| B1=6 | B2=5 | B3=2 | B4=4 |
| 10-5 | 10-6 | 10-7 | 10-8 |
| B5=4 | B6=0 | B7=3 | B8=7 |
| 10-9 | 10-10 | 10-11 | 10-12 |
| B9=5 | B10=2 | B11=1 | B12=5 |
| 10-13 | 10-14 | 10-15 | 10-16 |
| B13=1 | B14=4 | B15=3 | B16=5 |

Figure 5

| 10-1 | 10-2 | 10-3 | 10-4 |
|---|---|---|---|
| Δ1=−1 | Δ2=0 | Δ3=+3 | Δ4=+2 |
| 10-5 | 10-6 | 10-7 | 10-8 |
| Δ5=+2 | Δ6=+5 | Δ7=+2 | Δ8=−2 |
| 10-9 | 10-10 | 10-11 | 10-12 |
| Δ9=0 | Δ10=+3 | Δ11=+4 | Δ12=0 |
| 10-13 | 10-14 | 10-15 | 10-16 |
| Δ13=+4 | Δ14=−1 | Δ15=+2 | Δ16=0 |

Figure 6

| 10-1 | 10-2 | 10-3 | 10-4 |
|---|---|---|---|
| B1=R | B2=U | B3=U | B4=U |
| 10-5 | 10-6 | 10-7 | 10-8 |
| B5=U | B6=U | B7=U | B8=D |
| 10-9 | 10-10 | 10-11 | 10-12 |
| B9=U | B10=U | B11=U | B12=U |
| 10-13 | 10-14 | 10-15 | 10-16 |
| B13=U | B14=U | B15=U | B16=U |

BIOSENSOR CALIBRATION SYSTEM AND RELATED METHOD

BACKGROUND

The semiconductor industry has experienced rapid growth due to improvements in the integration density of a variety of electronic components (e.g., transistors, diodes, resistors, capacitors, etc.). For the most part, this improvement in integration density has come from shrinking the semiconductor process node (e.g., shrinking the process node towards the sub-20 nm node). Another semiconductor industry experiencing rapid growth is the microelectromechanical systems (MEMS) industry. MEMS devices are found in a variety of applications, ranging from automotive electronics to smartphones, and even biomedical devices.

Biomedical MEMS (BioMEMS) devices perform a variety of functions. A pH sensor is one type of BioMEMS device that electronically determines pH of a solution in contact with the pH sensor. The pH sensor may be used in disease detection, organ tissue monitoring, water contamination identification, or myriad other practical applications.

BRIEF DESCRIPTION OF THE DRAWINGS

For a more complete understanding of the present embodiments, and the advantages thereof, reference is now made to the following descriptions taken in conjunction with the accompanying drawings, in which:

FIG. 5 is a diagram of the array after binary signals are generated and stored in accordance with various embodiments of the present disclosure;

FIG. 6 is a diagram showing adjustments generated by the correction factor generator for the biosensors of FIG. 5 based on the mode;

FIG. 7 is a diagram illustrating calibration of the array using one biosensor as a reference in accordance with various embodiments of the present disclosure.

DETAILED DESCRIPTION OF ILLUSTRATIVE EMBODIMENTS

The making and using of the present embodiments are discussed in detail below. It should be appreciated, however, that the present disclosure provides many applicable inventive concepts that can be embodied in a wide variety of specific contexts. The specific embodiments discussed are merely illustrative of specific ways to make and use the disclosed subject matter, and do not limit the scope of the different embodiments.

Embodiments will be described with respect to a specific context, namely calibration circuits for biosensors and related methods. Other embodiments may also be applied, however, to other types of calibration circuits and/or sensor circuits.

Throughout the various figures and discussion, like reference numbers refer to like objects or components. Also, although singular components may be depicted throughout some of the figures, this is for simplicity of illustration and ease of discussion. A person having ordinary skill in the art will readily appreciate that such discussion and depiction can be and usually is applicable for many components within a structure.

In the following disclosure, a novel calibration circuit and method are introduced. The calibration circuit uses a decision unit to calibrate an array of biosensors to have similar sensing characteristics.

Figure 1:
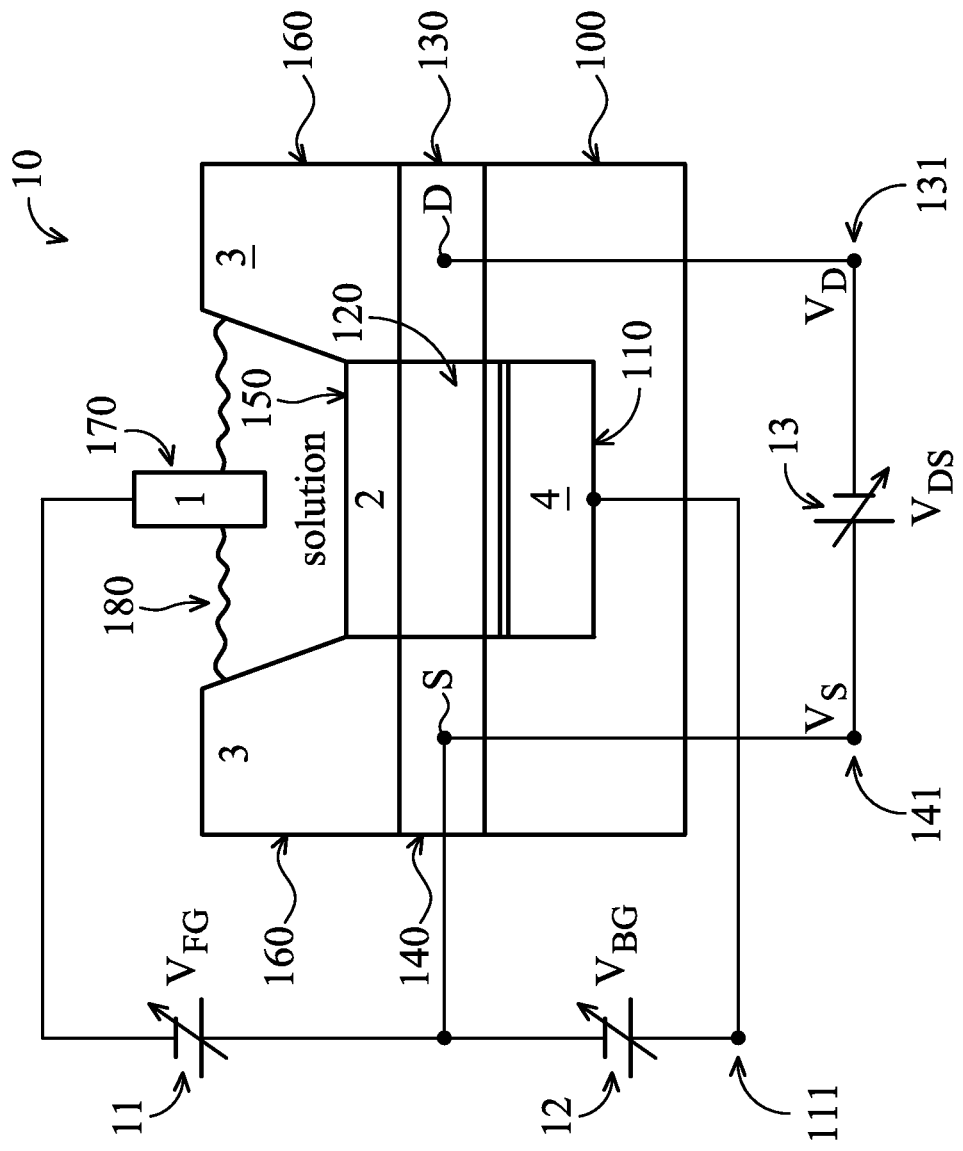
FIG. 1 is a diagram of a semiconductor device in accordance with various embodiments of the present disclosure.

Referring now to FIG. 1, illustrated is a semiconductor device 10. In some embodiments, the semiconductor device 10 is a BioFET device (biologically sensitive field-effect transistor, or bio-organic field-effect transistor). The semiconductor device 10 includes a gate structure 110 formed on substrate 100. The substrate 100 further includes a source region 140, a drain region 130, and an active region 120 (e.g., including a channel region) interposing the source region 140 and the drain region 130. The gate structure 110, the source region 140, the drain region 130, and the active region 120 may be formed using suitable CMOS process technology. The gate structure 110, the source region 140, the drain region 130, and the active region 120 form a FET. An isolation layer 160 is disposed on the opposing side of the substrate 100, as compared to the gate structure 110 (i.e., backside of the substrate).

An opening 180 is provided in the isolation layer 160. The opening 180 is substantially aligned with the gate structure 110. An interface layer 150 (or "sensing film 150") may be disposed in the opening 180 on the surface of the active region 120. The interface layer 150 may be operable to provide an interface for positioning one or more receptors for detection of biomolecules or bio-entities.

The semiconductor device 10 includes electrical contacts to the source region 140 (node 141), the drain region 130 (node 131), the gate structure 110 (node 111), and/or the active region 120, the interface layer 150, or a reference electrode 170. The reference electrode 170 provides bias potential to turn on a front gate of the semiconductor device 10.

Thus, while a conventional FET (field-effect transistor) uses a gate contact to control conductance of the semiconductor between the source and drain (e.g., the channel), the semiconductor device 10 allows receptors formed on the opposing side of the FET device to control the conductance, while the gate structure 110 (e.g., polysilicon) provides a back gate (e.g., source substrate or body node in a conventional FET). The gate structure 110 provides a back gate that can control the channel electron distribution without a bulk substrate effect. Thus, if the receptors attach to a molecule provided on the interface layer 150 in the opening 180, the resistance of the field-effect transistor channel in the active region 120 is altered. Therefore, the semiconductor device 10 may be used to detect one or more specific biomolecules or bio-entities in the environment around and/or in the opening 180.

The semiconductor device 10 may include additional passive components such as resistors, capacitors, inductors, and/or fuses; and other active components, including P-channel field effect transistors (PFETs), N-channel field effect transistors (NFETs), metal-oxide-semiconductor field effect transistors (MOSFETs), complementary metal-oxidesemiconductor (CMOS) transistors, high voltage transistors, and/or high frequency transistors; other suitable components; and/or combinations thereof. It is further understood that additional features can be added in the semiconductor device 10, and some of the features described below can be replaced or eliminated, for additional embodiments of the semiconductor device 10.

Biasing voltage sources 11, 12, 13 are also shown in FIG. 1. The biasing voltage source 11 establishes a front gate voltage $V_{FG}$ from the source region 140 to the reference electrode 170. The biasing voltage source 12 establishes a back gate voltage $V_{BG}$ from the source region 140 to the gate structure 110. The biasing voltage source 13 establishes a drain-source voltage $V_{DS}$ from the drain region 130 to the source region 140.

Figure 2:
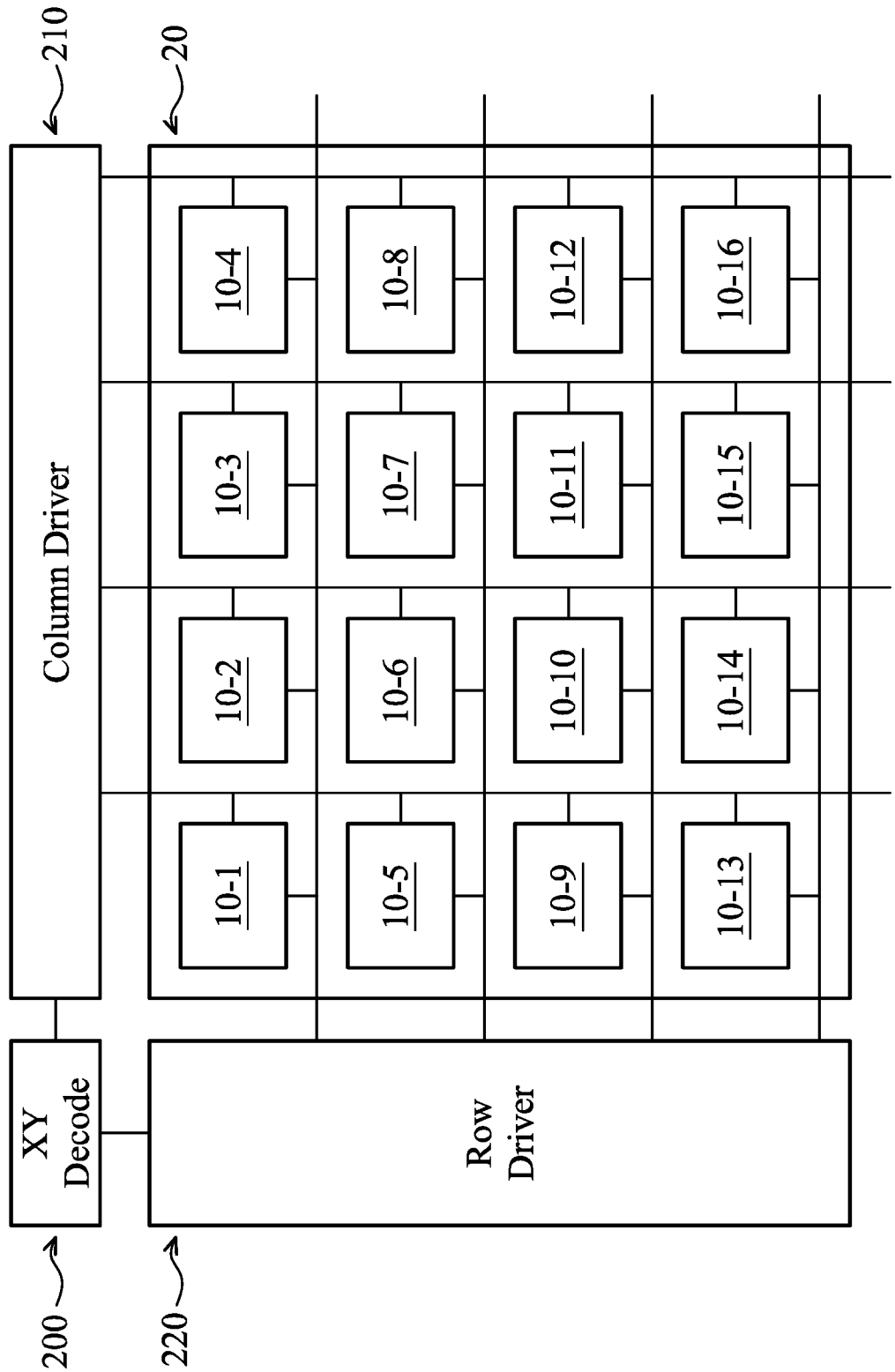
FIG. 2 is a diagram showing an array including at least two of the biosensor in accordance with various embodiments of the present disclosure.

FIG. 2 is a diagram showing an array 20 including at least two biosensors 10-1, 10-2, . . . , 10-16 substantially the same as the biosensor 10 in accordance with various embodiments of the present disclosure. In some embodiments, the biosensors 10-1, 10-2, . . . , 10-16 are arranged in a matrix. For example, the array 20 shown in FIG. 2 is a 4×4 matrix. In some embodiments, the array has more or fewer than the sixteen biosensors 10-1, 10-2, . . . , 10-16 shown in FIG. 2.

An XY decoder 200 converts an input address to a row signal and a column signal. The row signal is received by a row driver 220 electrically connected to each row of the array 20. The column signal is received by a column driver 210 electrically connected to each column of the array. In some embodiments, the row driver 220 generates the back gate voltage $V_{BG}$, and the column driver 210 generates the drain-source voltage $V_{DS}$.

In most applications, it is desirable for all biosensors 10-1, 10-2, . . . , 10-16 of the array 20 to generate a similar output current in the presence of any particular pH value. For example, all biosensors 10-1, 10-2, . . . , 10-16 of the array 20 should output a first current corresponding to a first pH value, and a second current corresponding to a second pH value. One approach for making the output currents of the biosensors 10-1, 10-2, . . . , 10-16 uniform is self-calibration. Prior to (or sometimes in line with) using the array 20 in a real application, the biosensors 10-1, 10-2, . . . , 10-16 of the array 20 are calibrated, e.g. by adjusting individual back gate voltages $V_{BG}$ applied to the biosensors 10-1, 10-2, . . . , 10-16. Changing the back gate voltages $V_{BG}$ applied affects sensitivity of the biosensors 10-1, 10-2, . . . , 10-16.

Figure 3:
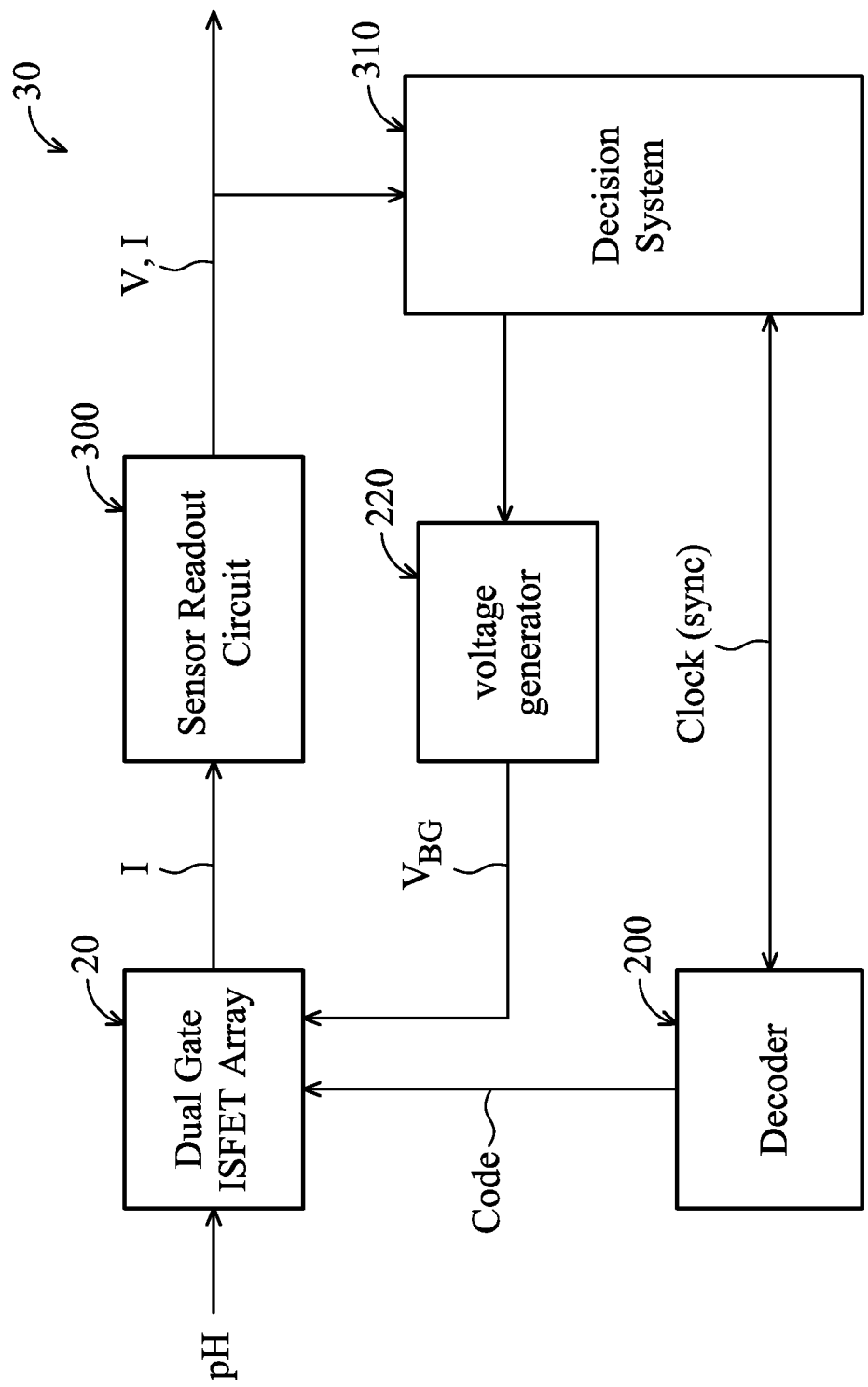
FIG. 3 is a circuit block diagram of a device with self-calibration in accordance with various embodiments of the present disclosure.

FIG. 3 is a circuit block diagram of a device 30 with self-calibration in accordance with various embodiments of the present disclosure. The device 30 includes the array 20 of FIG. 2. A sensor readout circuit 300 senses output signals (e.g., drain currents) of the biosensors 10 of the array 20 generated in response to, for example, pH of the solution. In some embodiments, the output signals are sensed sequentially by the sensor readout circuit 300. In some embodiments, the output signals are sensed simultaneously by the sensor readout circuit 300. The sensor readout circuit 300 generates a readout signal (e.g., voltage, current) based on the output signal(s). In some embodiments, the readout signal is an amplified version of an individual output signal of the output signals.

A decision system 310 receives the readout signal from the sensor readout circuit 300. The decision system 310 is synchronized with the XY decoder 200 by a clock signal. For example, the biosensor 10-1 is selected by the XY decoder 200 and read by the sensor readout circuit 300 in a same clock period. In some embodiments, the decision system 310 receives a first output signal corresponding to a first biosensor of the array 20, stores the first output signal, and subsequently receives a second output signal corresponding to a second biosensor of the array 20. The decision system 310 compares the first output signal with the second output signal, and generates a difference signal having magnitude proportional (e.g., equal) to a difference between the first output signal and the second output signal. For example, if the second output signal is larger than the first output signal, the difference signal may have a negative value. If the second output signal is smaller than the first output signal, the difference signal may have a positive value.

In some embodiments, the row driver 220 (or "voltage generator 220") is tuned based on the difference signal. In some embodiments, the row driver 220 outputs a baseline (or default) back gate voltage $V_{BG-ORG}$ that is modified on an individual basis (per biosensor 10 of the array 20) by the difference signal outputted by the decision system 310. In some embodiments, the baseline back gate voltage $V_{BG-ORG}$ is a predetermined voltage set by, for example, a designer, system integrator, end user, or the like. In some embodiments, the baseline back gate voltage $V_{BG-ORG}$ is a lowest back gate voltage $V_{BG-MIN}$ corresponding to a biosensor 10 having highest sensitivity. In some embodiments, the baseline back gate voltage $V_{BG-ORG}$ is a mean (average) voltage $V_{BG-AVG}$ corresponding to an average sensitivity of all biosensors 10-1, 10-2, . . . , 10-16 of the array 20.

Figure 4:
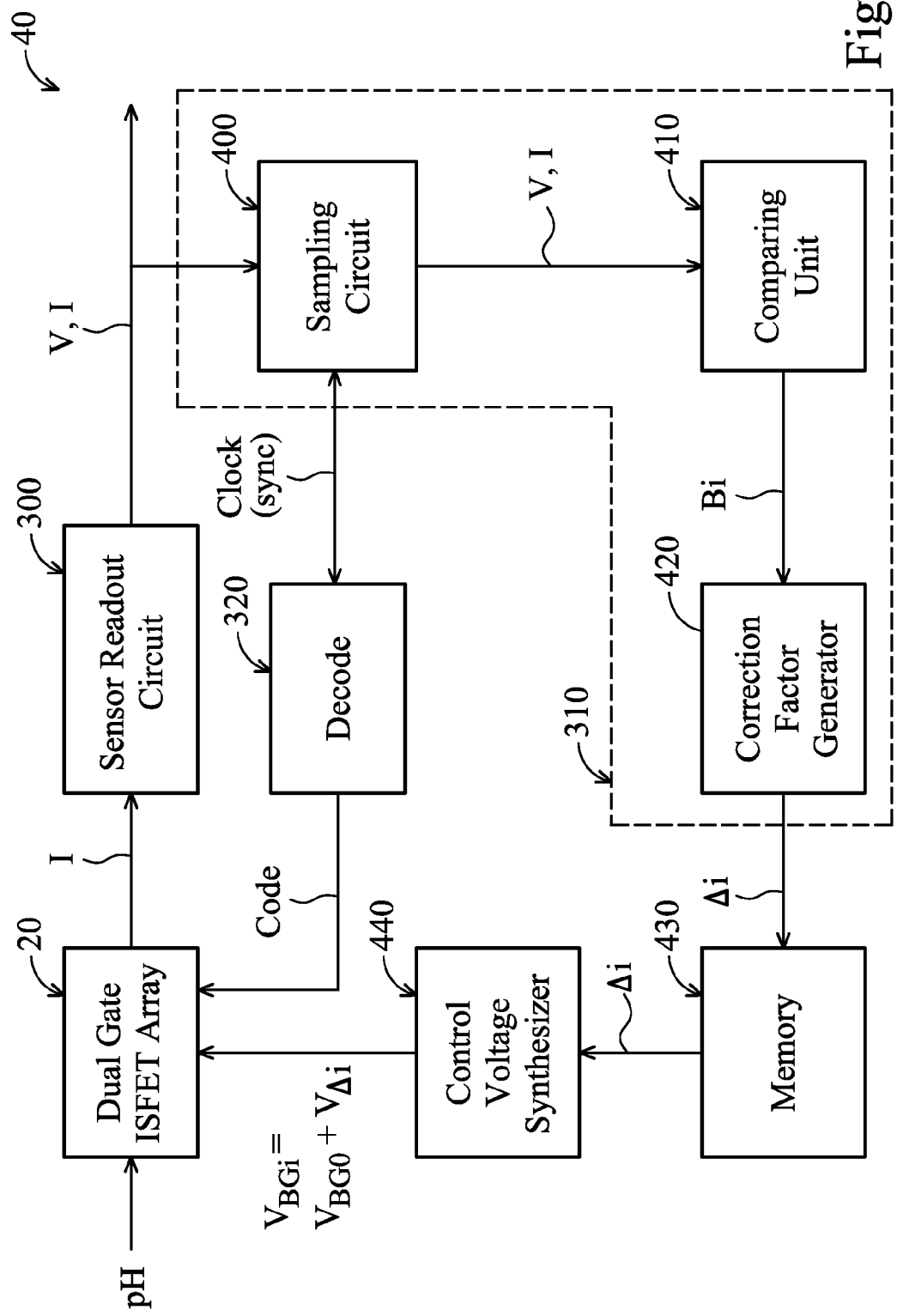
FIG. 4 is a detailed circuit block diagram showing a device with self-calibration in accordance with various embodiments of the present disclosure.

FIG. 4 is a detailed circuit block diagram showing a device 40 with self-calibration in accordance with various embodiments of the present disclosure. The device 40 is similar in many respects to the device 30, with like reference numerals representing like components. In some embodiments, the decision system 310 includes a sampling circuit 400, a comparing unit 410, and a correction factor generator 420. In some embodiments, the device 40 further includes memory 430 and a control voltage synthesizer 440.

The sampling circuit 400 includes at least one sampling unit. In sync with the clock signal, the sampling circuit 400 samples output of the sensor readout circuit 300. In some embodiments, the sampling circuit 400 includes at least one sample-and-hold circuit. In some embodiments, a charge storing element of the sampling circuit 400 is charged by the output of the sensor readout circuit 300 in a high phase of the clock signal to have a stored value. The charge storing element is then isolated from the sensor readout circuit 300 in a low phase of the clock signal. In some embodiments, the sampling circuit 400 stores a first voltage of the output of the sensor readout circuit 300 in a first high phase, then stores a second voltage of the output of the sensor readout circuit 300 in a second high phase subsequent to the first high phase. The first voltage may correspond to a first biosensor 10-1 of the array 20, and the second voltage may correspond to a second biosensor 10-2 of the array (as shown in FIG. 5).

The comparing unit 410 receives the stored value of the sampling circuit 400, and converts the stored value to a digital signal. In some embodiments, the comparing unit 410 outputs a binary signal Bi based on a fixed reference. For example, if the device 40 operates on a 5 Volt power supply, a stored value of 5 Volts may be converted to a digital signal having binary value "111," a stored value of 2.5 Volts may correspond to a binary value "100," and a stored value of 0 Volts may correspond to a binary value "000." In some embodiments, the comparing unit 410 includes at least an analog-to-digital converter (ADC). In some embodiments, the ADC is a simple ADC having resolution lower than about 6 bits. In some embodiments, the ADC has resolution of 3 bits or lower. The comparing unit 410 outputs the binary signal Bi corresponding to the output of the biosensor 10 being sensed. For example, a binary signal B1 is a digital representation of current output of the biosensor 10-1 in response to pH of the solution in an opening 180-1 of the biosensor 10-1.

In some embodiments, one of the biosensors 10-1, 10-2, ..., 10-16 is used to generate a reference value by which others of the biosensors 10-1, 10-2, ..., 10-16 are compared. For example, the biosensor 10-1 may be used as a reference for generating the binary signals B2-B16. In another example, the biosensor 10-7 may be used as a reference for generating the binary signals B1-B6, B8-B16. The comparing unit 410 may store a reference voltage corresponding to the biosensor 10-1 (for example) in a first clock cycle. Then, the binary signals B2-B16 are generated by determining whether output current of each corresponding biosensor 10-2, 10-3, ..., 10-16 is greater than or less than output current of the first biosensor 10-1.

Shown in FIG. 5, after reading all biosensors 10-1, 10-2, ..., 10-16 of the array 20, binary signals B1-B16 are generated and stored. Values of the binary signals B1-B16 shown in FIG. 5 may represent decimal numbers corresponding to 3-bit binary numbers outputted by the comparing unit 410. For purposes of illustration, the array 20 shown in FIG. 5 has a statistical mean of about 3.6, a statistical median of 4, and statistical modes of 4 and 5. In some embodiments, the self-calibration includes global calibration (array-level), local calibration (biosensor-level), a combination thereof, or the like. As an example of global calibration, in some embodiments, the mean (3.6 in FIG. 5) is used to select a global back gate voltage $V_{BG}$ applied to all of the biosensors 10-1, 10-2, ..., 10-16.

In some embodiments, local calibration is performed to adjust the back gate voltage $V_{BG}$ applied to each of the biosensors 10-1, 10-2, ..., 10-16. In some embodiments, the mode is used as a reference for adjusting the biosensors 10-1, 10-2, ..., 10-16 of the array 20. In some embodiments, the median is used as a reference for adjusting the biosensors 10-1, 10-2, ..., 10-16.

FIG. 6 is a diagram showing adjustments Δ1-Δ16 generated by the correction factor generator 420 for the biosensors 10-1, 10-2, ..., 10-16 of FIG. 5 based on a mode (e.g., 5). When multiple modes exist, a selected mode can be a largest, smallest, middle or other mode of the multiple modes. In some embodiments, the correction factor generator 420 includes a digital adder, a digital subtractor, or the like. In some embodiments, the adjustments Δ1-Δ16 are digital signals. For example, the adjustment Δ1 corresponding to the biosensor 10-1 is equal to a difference between the selected mode and the binary signal B1 (5−6=−1). The adjustment Δ3 corresponding to the biosensor 10-3 equals +3 (5−2=3). In some embodiments, differences between the median and the binary signals B1-B16 are used to generate the corresponding adjustments Δ1-Δ16.

FIG. 7 is a diagram illustrating calibration of the array 20 using the biosensor 10-1 as a reference in accordance with various embodiments of the present disclosure. In some embodiments, the biosensor 10-1 (or another of the biosensors 10-2, 10-3, ..., 10-16) is selected as a reference for calibrating remaining biosensors of the array 20. In some embodiments, the binary signals B2-B16 are 1-bit binary signals (e.g., 1 or 0) indicating whether to adjust up (U) or down (D) based on comparison with the reference biosensor (e.g., the biosensor 10-1). Taking the configuration of FIG. 5 as an example, the biosensor 10-1 is the second most sensitive biosensor of the array 20. As a result, only the biosensor 10-8 generates a binary signal B8 corresponding to a down adjustment when compared with output voltage sampled for the reference biosensor. Other biosensors 10-2, 10-3, ..., 10-7, 10-9, 10-10, ..., 10-16 generate binary signals B2-B7, B9-B16 corresponding to an up adjustment when compared with the output voltage sampled for the reference biosensor. In some embodiments, the adjustments shown in FIG. 5 are generated in a first calibration pass. In some embodiments, multiple iterative passes are used to make output responses of the biosensors 10-1, 10-2, ..., 10-16 (based on applied back gate voltages $V_{BG}$) substantially uniform (within one bit of resolution). In some embodiments, the multiple iterative passes increase/decrease the back gate voltages $V_{BG}$ by one in each pass. In some embodiments, the multiple iterative passes increase/decrease the back gate voltages $V_{BG}$ using a binary scheme. For example, the first pass may include an increase/decrease of 4, a second pass may include an increase/decrease of 2, and a third pass may include an increase/decrease of 1.

Referring once again to FIG. 4, in some embodiments, the adjustments Δ1-Δ16 are stored in the memory 430. In some embodiments, the memory 430 is read-only memory. In some embodiments, the memory 430 is one-time programmable (OTP) memory, such as an e-fuse array. In some embodiments, the memory 430 is multiple-times programmable (MTP) memory, such as embedded flash, or the like.

The control voltage synthesizer 440 generates back gate bias voltages $V_{BGi}$ applied to the biosensors 10-1, 10-2, ..., 10-16 based on the adjustments Δ1-Δ16 stored in the memory 430. In some embodiments, the control voltage synthesizer 440 includes a digital-to-analog converter (DAC). Each back gate bias voltage $V_{BGi}$ is equal to a default back gate bias voltage $V_{BG0}$ plus a corresponding adjustment voltage $V_{Ai}$. For example, the default back gate bias voltage $V_{BG0}$ may be a first voltage (e.g., −0.4 Volts), and adjustment voltages $V_{Ai}$ may have resolution of 0.1 Volts and range from 0 Volts to about 0.8 Volts. Using these parameters, the back gate bias voltages $V_{BG1}$-$V_{BG16}$ are in a range of about −0.4 Volts to about +0.4 Volts. In some embodiments, other voltages are used for the first voltage, the resolution, and the range of the adjustment voltages $V_{Ai}$. For example, the first voltage may be −0.8 Volts, the resolution may be 0.1 Volts, and the range may be from 0 to 0.8 Volts (e.g., for a 4-bit comparing unit 410 outputting 16 possible binary signals).

Figure 8:
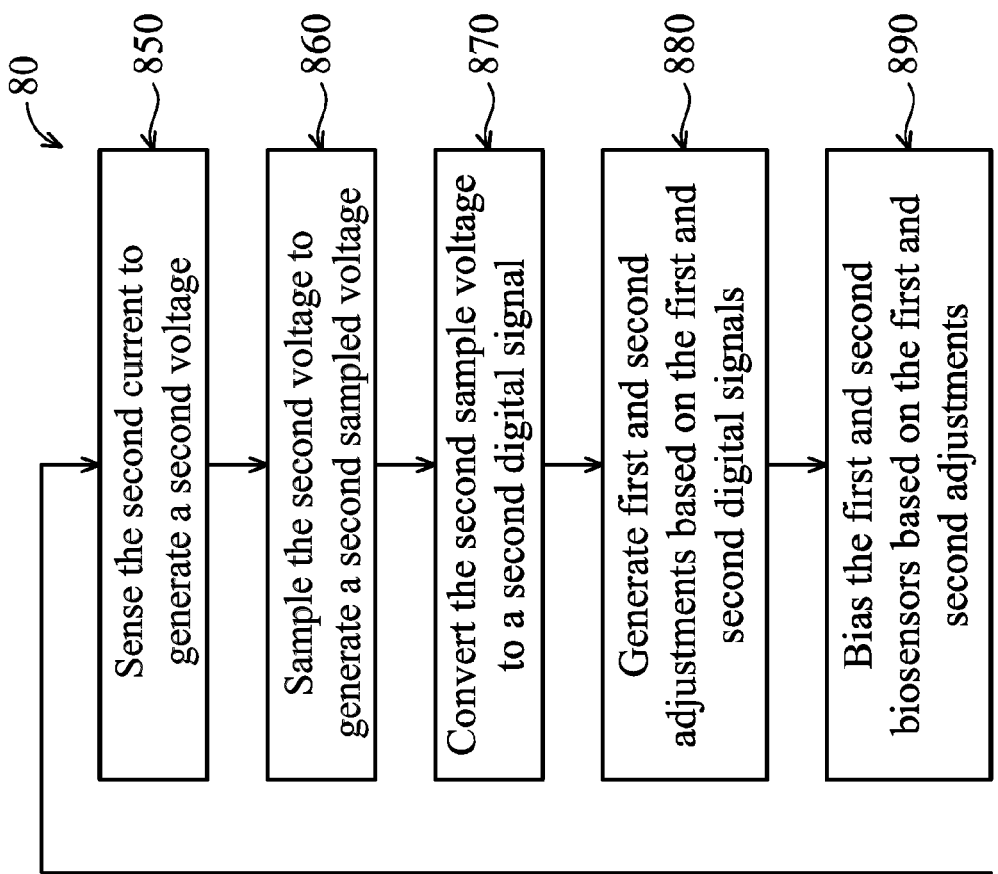
FIG. 8 is a flowchart of a method in accordance with various embodiments of the present disclosure.
Figure 8:
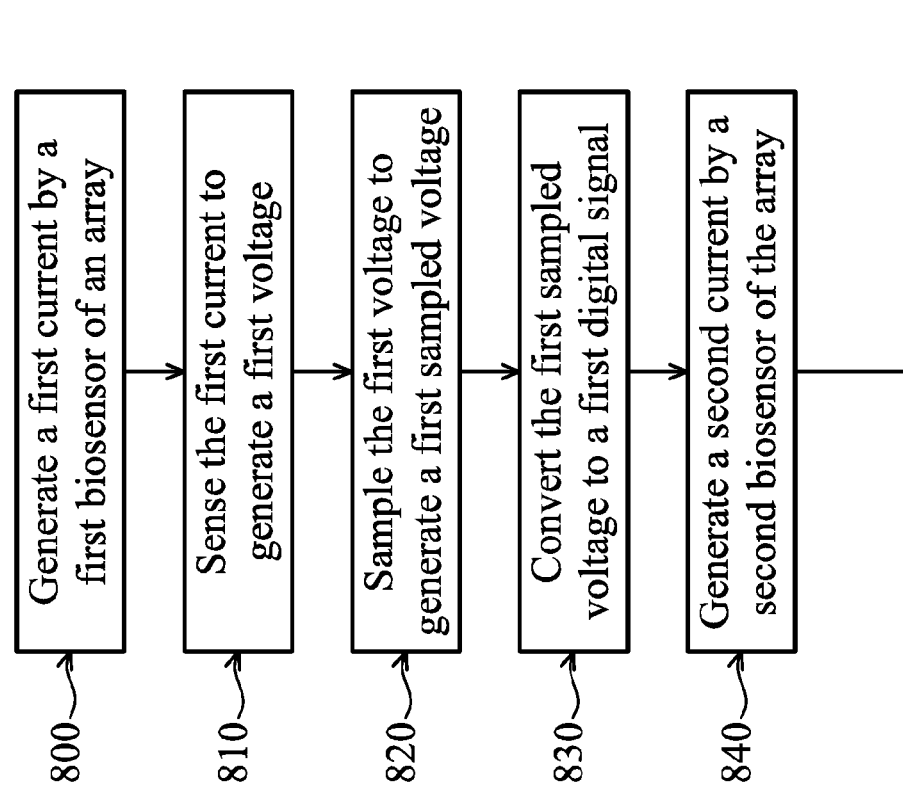

FIG. 8 is a flowchart of a method 80 in accordance with various embodiments of the present disclosure. In some embodiments, the method 80 is performed by the device 30 or the device 40. A first current (e.g., a drain current of an ISFET) is generated 800 by a first biosensor of an array of biosensors. In some embodiments, the first current is generated 800 in response to biasing including, for example, back gate, front gate, and drain-source voltage biasing. The first current is sensed 810 to generate a first voltage. In some embodiments, the sensing 810 includes conversion of the first current to the first voltage. In some embodiments, the sensing 810 further includes amplification. The first voltage is sampled 820 to generate a first sampled voltage. In some embodiments, the sampling 820 is performed by a sample-and-hold circuit including switches and at least one charge storing element (e.g., a capacitor). The first sampled voltage is converted 830 to a first digital signal (e.g., the binary signal B1).

A second biosensor of the array generates 840 a second current. In some embodiments, the second current is a drain current of an ISFET. In some embodiments, the second current is generated 840 in response to biasing including, for example, back gate, front gate, and drain-source voltage biasing. The second current is sensed 850 to generate a second voltage. In some embodiments, the sensing 850 includes conversion of the second current to the second voltage. In some embodiments, the sensing 850 further includes amplification. The second voltage is sampled 860 to generate a second sampled voltage. In some embodiments, the sampling 860 is performed by the sample-and-hold circuit. The second sampled voltage is converted 870 to a second digital signal (e.g., the binary signal B2).

In some embodiments, operations 840-870 are repeated for other biosensors of the array. In some embodiments, all digital signals associated with the biosensors of the array are stored in memory for further processing. For example, at least one adjustment is generated 880 based on the first and second digital signals. In some embodiments, all adjustments associated with the biosensors of the array are generated based on all digital signals (e.g., the binary signals B1-B16) associated with the biosensors. As described above with relation to FIGS. 5-7, in some embodiments, the adjustments are generated 880 using one of the biosensors (e.g., the biosensor 10-1) as a reference for calibrating other biosensors (e.g., the biosensors 10-2, 10-3, . . . , 10-16) of the array. In some embodiments, the adjustments are generated 880 using all of the biosensors of the array, for example, by using the statistical mean, median, or mode associated with the binary signals B1-B16. In some embodiments, the adjustments are stored in memory (e.g., read-only memory, flash memory, other non-volatile memory, or the like).

At least one biosensor of the array (e.g., the second biosensor 10-2) is biased 890 based on the at least one adjustment (e.g., the adjustment Δ2). In some embodiments, the biasing 890 is accomplished by a control voltage synthesizer that adds a number of adjustment voltages (e.g., 0.1 Volts) equal to the adjustment associated with one of the biosensors to a default bias voltage. In some embodiments, the default bias voltage is the back gate voltage $V_{BG}$. In some embodiments, some or all of the adjustments are zero (no adjustment).

Embodiments may achieve advantages. The devices 30, 40 have self-calibration that allows each biosensor of the array 20 to be biased in such a way that current distribution based on pH of the solution is uniform across the array 20. Resolution of the biosensors is also increased. Experimental data indicates that resolution below 0.02 pH is achieved by the devices 30, 40.

In accordance with various embodiments of the present disclosure, a device includes a first biosensor of a biosensor array, a second biosensor of a biosensor array, a readout circuit electrically connected to the biosensor array, a decoder electrically connected to the biosensor array, a voltage generator electrically connected to the biosensor array, and a decision system electrically connected to the voltage generator and the readout circuit.

In accordance with various embodiments of the present disclosure, a method includes (a) generating a first current by a first biosensor of an array; (b) sensing the first current to generate a first voltage; (c) sampling the first voltage to generate a first sampled voltage; (d) converting the first sampled voltage to a first digital signal; (e) generating a second current by a second biosensor of the array; (f) sensing the second current to generate a second voltage; (g) sampling the second voltage to generate a second sampled voltage; (h) converting the second sampled voltage to a second digital signal; (i) generating at least one adjustment based on the first and second digital signals; and (j) biasing at least one biosensor of the array based on the at least one adjustment.

As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising". Moreover, the term "between" as used in this application is generally inclusive (e.g., "between A and B" includes inner edges of A and B).

Although the present embodiments and their advantages have been described in detail, it should be understood that various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods, and steps described in the specification. As one of ordinary skill in the art will readily appreciate from the disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A device comprising:
    a first biosensor of a biosensor array, the first biosensor configured to generate a first current in response to being biased at a first back gate voltage;
    a second biosensor of the biosensor array, the second biosensor configured to generate a second current in response to being biased at a second back gate voltage;
    a decision system configured to determine a first adjustment based on the first current and a reference and generate a second adjustment based on the second current and the reference; and
    a voltage generator electrically connected to the decision system and the biosensor array and configured to adjust the first back gate voltage of the first biosensor based on the first adjustment and adjust the second back gate voltage of the second biosensor based on the second adjustment.

2. The device of claim 1, wherein the decision system comprises:
    a sampling circuit configured to sample a first voltage based on the first current to generate a first sampled voltage and sample a second voltage based on the second current to generate a second sampled voltage;
    a comparing unit electrically connected to the sampling circuit and configured to:
        convert the first sampled voltage to a first digital signal and convert the second sampled voltage to a second digital signal, and
        compare the first and second digital signals to the reference, respectively; and
    a correction factor generator electrically connected to the comparing unit and configured to determine the first and second adjustments based on the comparison.

3. The device of claim 2, further comprising:
non-volatile memory electrically connected to the correction factor generator and the voltage generator and configured to store the first and second adjustments.

4. The device of claim 3, wherein the non-volatile memory comprises:
a read-only memory.

5. The device of claim 3, wherein the comparing unit comprises:
an analog-to-digital converter configured to convert the first sampled voltage to the first digital signal and convert the second sampled voltage to the second digital signal.

6. The device of claim 1, wherein the reference is a voltage of a power supply on which the first and second biosensors operate.

7. The device of claim 1, wherein:
the first and second adjustments are digital signals; and
the voltage generator comprises:
a digital-to-analog converter configured to convert the first adjustment to a first adjustment voltage and convert the second adjustment to a second adjustment voltage.

8. The device of claim 1, wherein:
the first biosensor is a dual gate ion-sensitive field-effect transistor (ISFET); and
the second biosensor is a dual gate ISFET.

9. The device of claim 1, further comprising:
a readout circuit electrically connected to the biosensor array and the decision system and configured to sequentially generate a first value of a readout signal based on the first current and a second value of the readout signal based on the second current.

10. The device of claim 1, further comprising:
a readout circuit electrically connected to the biosensor array and the decision system and configured to simultaneously generate a first readout signal based on the first current and a second readout signal based on the second current.

11. The device of claim 10, wherein the readout circuit comprises an amplifier configured to amplify the first current to generate the first readout signal and amplify the second current to generate the second readout signal.

12. The device of claim 1, wherein the voltage generator is configured to simultaneously adjust the first back gate voltage of the first biosensor based on the first adjustment and adjust the second back gate voltage of the second biosensor based on the second adjustment.

13. The device of claim 1, wherein the voltage generator is configured to adjust the first back gate voltage of the first biosensor by modifying a baseline back gate voltage based on the first adjustment and adjust the second back gate voltage of the second biosensor by modifying the baseline back gate voltage based on the second adjustment.

14. The device of claim 1, further comprising:
a decoder electrically connected to the biosensor array and the decision system and configured to select one of the first and second biosensors based on an input address.

15. The device of claim 14, wherein the decoder is configured to select the one of the first and second biosensors in a same clock period in which the respective first or second current is sensed.

16. The device of claim 1, wherein the reference is determined based on one of the first and second currents.

17. The device of claim 16, wherein the one of the first and second currents corresponds to a second most sensitive biosensor of the biosensor array.

18. The device of claim 2, wherein the reference is a statistical mean, a statistical median, or a statistical mode of at least the first and second digital signals.

* * * * *